(12) United States Patent
Schwidder et al.

(10) Patent No.: US 10,739,242 B2
(45) Date of Patent: Aug. 11, 2020

(54) INFILTROMETER APPARATUS AND RELATED METHODS OF USE

(71) Applicant: UPSTREAM TECHNOLOGIES, INC., New Brighton, MN (US)

(72) Inventors: Arthur J. Schwidder, New Brighton, MN (US); Richard A. Kuntz, Big Lake, MN (US)

(73) Assignee: UPSTREAM TECHNOLOGIES, INC., New Brighton, MN (US)

( * ) Notice: Subject to any disclaimer, the term of this patent is extended or adjusted under 35 U.S.C. 154(b) by 102 days.

(21) Appl. No.: 15/660,883

(22) Filed: Jul. 26, 2017

(65) Prior Publication Data
US 2019/0033196 A1    Jan. 31, 2019

(51) Int. Cl.
*G01N 15/08*    (2006.01)
*G01N 33/24*    (2006.01)

(52) U.S. Cl.
CPC ....... *G01N 15/0806* (2013.01); *G01N 33/246* (2013.01)

(58) Field of Classification Search
CPC ............ G01N 15/0806; G01N 33/246; G01N 15/082; G01N 15/0826; G01N 2015/084; G01N 2015/0866; G01N 2015/0873; G01N 2033/245; G01F 23/14; G01F 23/16; G01F 23/162; G01F 23/164; A01G 27/008
USPC ................................ 73/38, 863.23, 301, 298
See application file for complete search history.

(56) References Cited

U.S. PATENT DOCUMENTS

| | | | | |
|---|---|---|---|---|
| 3,548,635 A | * | 12/1970 | Hutchinson | G01N 15/082 73/38 |
| 3,892,126 A | * | 7/1975 | Curtin | G01F 23/58 73/322 |
| 3,898,872 A | * | 8/1975 | Skaling | G01N 33/246 73/73 |
| 3,945,247 A | * | 3/1976 | Anderson | E02D 1/027 73/73 |
| 4,164,139 A | * | 8/1979 | Jones | G01N 33/42 73/38 |

(Continued)

OTHER PUBLICATIONS

Robichaud et al., "New Procedure for Sampling Infiltration to Assess Postfire Soil Water Repellency", Mar. 2003, Res. Note. RMRS-RN-33. Fort Collins, CO: U.S. Department of Agriculture, Forest Service, Rocky Mountain Research Station. 14 p (Year: 2008).*

(Continued)

*Primary Examiner* — Tran M. Tran
(74) *Attorney, Agent, or Firm* — Cradle Patent Law chtd

(57) ABSTRACT

In various aspects, the infiltrometer apparatus includes a cylinder that defines a cylinder passage coupleable to a base that defines a base passage to form an infiltrometer passage. The infiltrometer apparatus includes a baffle removably emplaced within the infiltrometer passage in gapped relation with a soil surface of a soil, in various aspects. In various aspects, the infiltrometer apparatus includes a level detector to detect a water surface level of a water surface within the infiltrometer passage. The level detector may communicate by network with a computer to communicate data indicative of the water surface level to the computer. The network may be wireless, at least in part. Related methods of use of the infiltrometer apparatus are also disclosed herein.

17 Claims, 5 Drawing Sheets

(56) References Cited

U.S. PATENT DOCUMENTS

| | | | | |
|---|---|---|---|---|
| 4,561,289 A * | 12/1985 | Jones | ............... | G01N 15/0806 73/38 |
| 4,587,857 A * | 5/1986 | Bush | ............... | G01N 33/24 175/226 |
| 4,884,436 A * | 12/1989 | Ankeny | ............... | G01N 15/0826 73/38 |
| 4,956,993 A * | 9/1990 | Mehler | ............... | G01N 15/08 73/38 |
| 4,979,390 A * | 12/1990 | Schupack | ............... | G01M 3/04 73/38 |
| 5,105,662 A * | 4/1992 | Marsh | ............... | G01F 23/162 73/299 |
| 5,157,959 A * | 10/1992 | Ankeny | ............... | G01N 33/24 73/38 |
| 5,345,820 A * | 9/1994 | Bernhardt | ............... | E21B 49/008 73/152.18 |
| 5,780,720 A * | 7/1998 | Swain | ............... | G01N 15/08 73/38 |
| 6,105,418 A * | 8/2000 | Kring | ............... | G01N 15/08 73/38 |
| 6,351,993 B1 * | 3/2002 | Schellenberg | ............... | G01F 23/162 73/290 R |
| 6,715,341 B2 * | 4/2004 | Bowen | ............... | G01N 15/08 73/37 |
| 6,718,835 B2 * | 4/2004 | Wang | ............... | E02D 1/027 73/38 |
| 6,742,405 B2 * | 6/2004 | Hubbell | ............... | E02D 1/06 73/863.23 |
| 6,810,755 B1 * | 11/2004 | Pask | ............... | G01N 15/0826 73/152.41 |
| 6,938,461 B1 * | 9/2005 | Johnson | ............... | E21B 49/00 73/37 |
| 7,059,174 B2 | 6/2006 | Ranjan et al. | | |
| 7,121,140 B2 * | 10/2006 | Lo | ............... | G01F 23/68 73/305 |
| 7,437,957 B2 * | 10/2008 | Jobin | ............... | A01G 25/167 73/73 |
| 7,631,545 B2 * | 12/2009 | Skaling | ............... | G01N 7/10 137/78.3 |
| 8,381,582 B2 * | 2/2013 | Dahan | ............... | G01N 33/246 73/152.25 |
| 8,650,948 B2 * | 2/2014 | Lee | ............... | G01F 1/00 702/45 |
| 8,714,181 B2 * | 5/2014 | Shani | ............... | G01N 7/10 137/78.3 |
| 8,756,991 B2 * | 6/2014 | Edwards | ............... | G01F 23/185 73/290 R |
| 8,909,484 B2 * | 12/2014 | Farsad | ............... | G01N 11/00 702/25 |
| 9,371,729 B2 * | 6/2016 | Brown | ............... | G01N 33/24 |
| 9,395,307 B2 * | 7/2016 | Harada | ............... | G01N 21/85 |
| 9,606,027 B2 * | 3/2017 | Kucza | ............... | G01N 33/246 |
| 9,645,069 B2 * | 5/2017 | Matsukata | ............... | G01N 15/088 |
| 2009/0038390 A1 | 2/2009 | Dahan | | |
| 2013/0080074 A1 | 3/2013 | Farsad et al. | | |

OTHER PUBLICATIONS

Web Page, Upstream Technologies Inc., Mar. 23, 2016.
Suleman Mandra, Lab #7 Infiltration and Infiltrometers for Measurement of Soil Intake Properties, Environmental Measurements CE/ENVE 320-04.
F. Ahmed et al., A Modified Philip_Dunne Infiltrometer for Measuring the Field-Saturated Hydraulic Conductivity of Surface Soil, Vadose Zone J., Soil Science Society of America, Oct. 14, 2014.

* cited by examiner

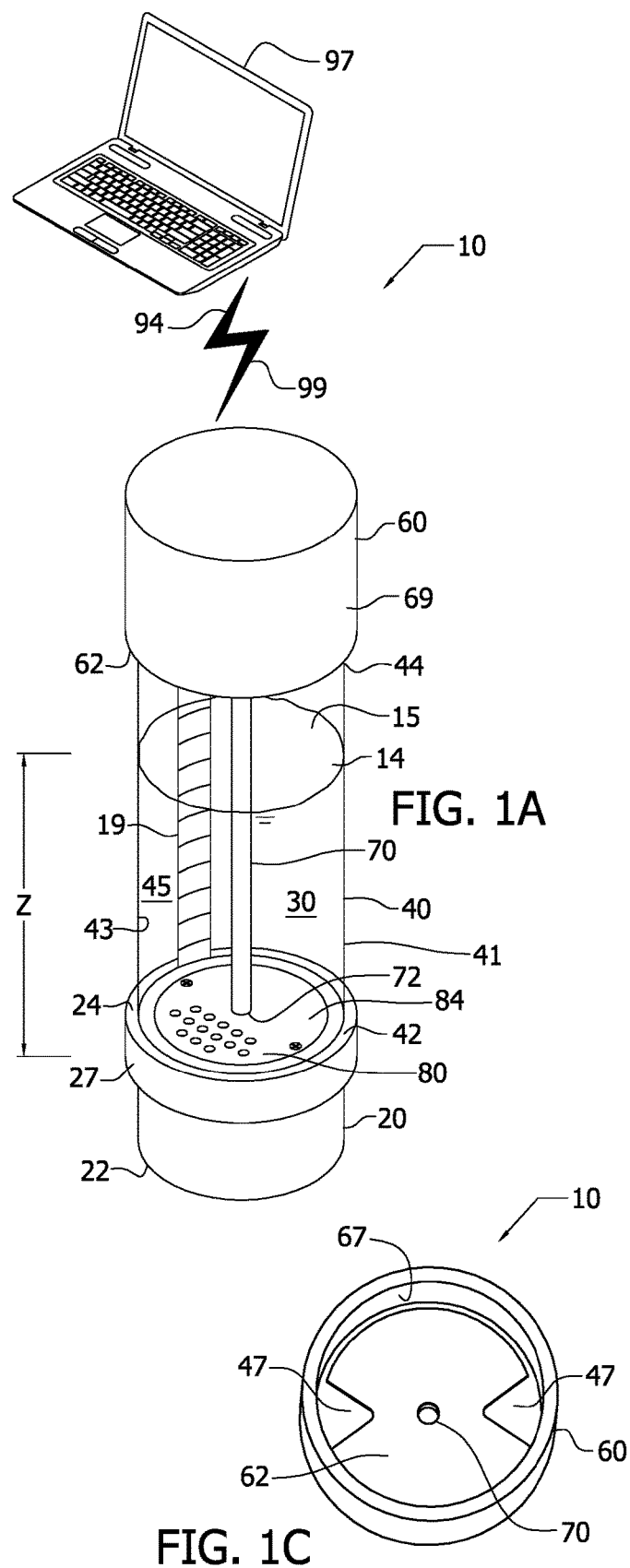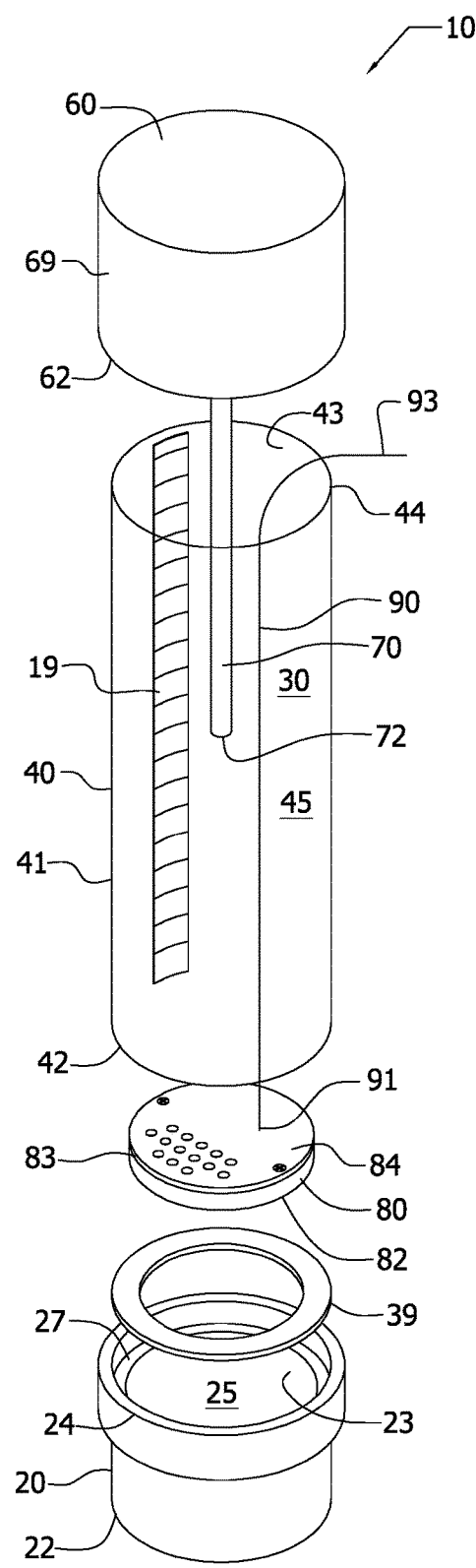

INFILTROMETER APPARATUS AND RELATED METHODS OF USE

BACKGROUND OF THE INVENTION

Field

The present disclosure relates to infiltrometers for measurement of soil properties, and, in particular, to single ring and falling head infiltrometers.

Background

An infiltrometer device is used to measure the rate of water infiltration into soil, in various aspects. Various soil properties of the soil may be determined from the rate at which water infiltrates into the soil as measured using the infiltrometer. These soil properties may be used for many purposes such as, for example, sizing, design, building, testing and maintenance of rain gardens (e.g. infiltration ponds, catch basins, bioretention areas), estimation of runoff from precipitation events, optimization of irrigation, design of drainage systems, design of reservoirs, erosion control, design of waste disposal systems (e.g. septic systems, sewage lagoons, landfills, drain fields), and estimation of the transport of various material within the soil. Accordingly, it may be important to accurately measure the rate at which water infiltrates into the soil in order to accurately determine the soil properties.

Soil, as used herein, includes soil as well as other porous media. Soil properties, as used herein, may include, for example, porosity, sorptivity, hydraulic conductivity, and intrinsic permeability. Soil properties may include, for example, parameters used in various infiltration models such as, for example, the Lewis equation, Horton's equation, Phillip's equation, Green-Ampt model, Philip Dunne equation, and modified Philip Dunne equation (MPD).

An infiltrometer device may be formed, for example, as a single ring that defines an infiltrometer passage. An end of the infiltrometer device is inserted into the soil, and water is then added into the infiltrometer passage. Following the addition of the water, the decrease of the water surface of the water within the infiltrometer passage with respect to time (i.e. falling head) is observed and recorded. The observed decrease of the water surface with respect to time may then be used to determine soil properties of the soil.

However, it may be observed that the addition of water into the infiltrometer passage may disturb the soil proximate the soil surface. For example, particles proximate the soil surface may be suspended into the water by turbulence created by the addition of water into the infiltrometer passage. Larger or denser suspended particles may then precipitate out of the water back onto the soil surface prior to the precipitation of smaller or lighter particles effectively sorting particles proximate the soil surface thereby disturbing the soil. Such sorting may introduce error into the soil properties, which are now disturbed, as determined using infiltrometer devices. A baffle in contact with the soil surface may prevent suspension of particles, but the baffle may also interfere with water infiltration into the soil thus introducing error into the soil properties determined using the infiltrometer device.

In addition, observation of the decrease of the water surface level by a user may be subject to error leading to errors in the soil properties determined using the infiltrometer device. Calculation of soil properties from the observed decrease of the water surface level may be laborious. Even when automated, such calculations may be subject to data input errors leading to errors in the soil properties so calculated. Accordingly, there is a need for improved apparatus as well as related methods of use for the determination of soil properties.

BRIEF SUMMARY OF THE INVENTION

These and other needs and disadvantages may be overcome by the apparatus and related methods of use disclosed herein. Additional improvements and advantages may be recognized by those of ordinary skill in the art upon study of the present disclosure.

An infiltration apparatus is disclosed herein. In various aspects, the infiltrometer apparatus includes a cylinder that defines a cylinder passage coupleable to a base that defines a base passage to form an infiltrometer passage. The infiltrometer apparatus includes a baffle removably emplacable within the infiltrometer passage, in various aspects. The baffle is in gapped relation with a soil surface of a soil when the base coupled to the cylinder is inserted into the soil and the baffle is emplaced within the infiltrometer passage, in various aspects. The baffle may prevent disturbance of the soil by the addition of water into the infiltrometer passage, and the baffle does not disturb the soil by virtue of being in gapped relation with the soil, in various aspects.

In various aspects, the infiltrometer apparatus includes an assembly removably coupleable to a second cylinder end of the cylinder opposite the base, the assembly comprising a level detector to detect a water surface level of a water surface within the infiltrometer passage. The level detector may communicate by network with a computer to communicate data indicative of the water surface level to the computer. The network may be wireless, at least in part. Related methods of use of the infiltrometer apparatus are also disclosed herein.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

BRIEF DESCRIPTION OF THE DRAWINGS

FIG. 1A illustrates by perspective view an exemplary implementation of an infiltrometer apparatus;

FIG. 1B illustrates by exploded perspective view the exemplary infiltrometer apparatus of FIG. 1A;

FIG. 1C illustrates by perspective view portions of the exemplary infiltrometer apparatus of FIG. 1A;

Figure 2:
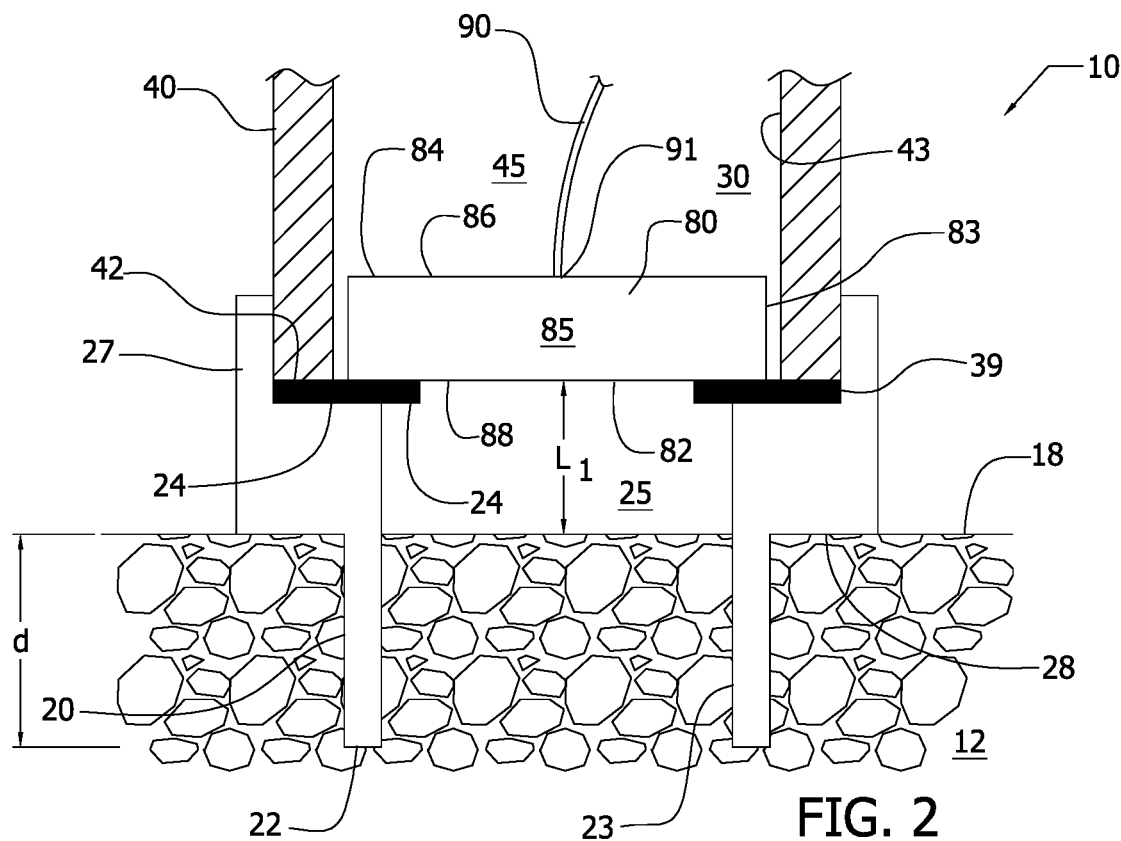
FIG. 2 illustrates by cut-away elevation view portions of the exemplary infiltrometer apparatus of FIG. 1A.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

In various aspects, the infiltrometer apparatus disclosed herein includes a cylinder with a cylinder end thereof coupled to a base to define an infiltrometer passage. The infiltrometer apparatus includes a baffle that is removably emplacable within the infiltrometer passage and offset from a soil surface of a soil by a gap when the base is inserted into the soil, in various aspects. The baffle may prevent disturbance of the soil surface during addition of water into the infiltrometer passage. Disturbance of the soil, as used herein, may include, for example, sorting of soil particles, disruption of soil structures, and the formation or destruction of flow pathways within the soil.

In various aspects, the infiltrometer apparatus disclosed herein includes an assembly removably coupleable to a second cylinder end of the cylinder opposite the base. The assembly may include at least portions of a level detector that detects a water surface level of a water surface within the infiltrometer passage. The level detector may detect variations of the water surface level within the infiltrometer passage over time, and the level detector may be linked by network with a computer to communicate data indicative of the water surface level to the computer. The computer may analyze the data to determine soil properties of the soil, and the computer may cooperate with the level detector in analyzing the data. The network may be implemented wirelessly, at least in part.

Apparatus, related methods of use, and related compositions of matter disclosed herein may be implemented, at least in part, in software having the form of computer readable instructions operably received by one or more computers to cause, at least in part, the one or more computers to function as at least a portion of the apparatus or to implement at least some of the steps of the methods of use. The methods of use disclosed herein may be implemented, at least in part, as a combination of hardware and operatively received software, in various aspects. Compositions of matter disclosed herein include non-transient computer readable media operably received by the one or more computers to cause the one or more computers, at least in part, to function as at least portions of the apparatus or to implement, at least in part, steps of the methods of use.

A computer, as used herein, includes, a processor that may execute computer readable instructions operably received thereby. The computer may be, for example, a single-processor computer, multiprocessor computer, multi-core computer, minicomputers, mainframe computer, supercomputer, distributed computer, personal computer, hand-held computing device, tablet, smart phone, or a virtual machine, and the computer may include several processors in networked communication with one another. The computer may include memory, screen, keyboard, mouse, storage devices, I/O devices, and so forth, in various aspects, and the computer may be operably connected to a network. The computer may execute various operating systems (OS) such as, for example, Microsoft Windows, Linux, UNIX, MAC OS X, real time operating system (RTOS), VxWorks, INTEGRITY, Android, iOS, or a monolithic software or firmware implementation without a defined traditional operating system.

Network, as used herein, may include the Internet cloud, as well as other networks of local to global scope. The network may include, for example, data storage devices, input/output devices, routers, databases, computers including servers, mobile devices, wireless communication devices, cellular networks, optical devices, cables, and other hardware and operable software, as would be readily recognized by those of ordinary skill in the art upon study of this disclosure. Network may be wired (e.g. optical, electromagnetic), wireless (e.g. infra-red (IR), electromagnetic), or a combination of wired and wireless, and the network may conform, at least in part, to various standards, (e.g. Bluetooth®, ANT, ZigBee, FDDI, ARCNET IEEE 802.11, IEEE 802.20, IEEE 802.3, IEEE 1394-1995, USB).

FIGS. 1A, 1B, and 1C illustrate exemplary infiltrometer apparatus 10 including base 20, cylinder 40, and assembly 60. As illustrated, base detent 27 disposed about base end 24 of base 20 and assembly arm 67 disposed about assembly side 62 of assembly 60 (see FIG. 4) receive cylinder end 42 and second cylinder end 44 of cylinder 40, respectively. Cylinder end 42 of cylinder 40 is coupled with base detent 27 proximate base end 24 of base 20. In some implementations, cylinder end 42 may be permanently coupled to base 20 by adhesive. In other implementations, cylinder end 42 may be removably coupled to base 20, for example, by frictional engagement, threaded engagement, or snappable engagement. Second cylinder end 44 of cylinder is removably engaged proximate assembly arm 67 on assembly side 62 of assembly 60, in this implementation.

Inner surface 43 of cylinder 40 defines cylinder passage 45 between cylinder end 42 and second cylinder end 44, inner surface 23 of base 20 defines base passage 25 (also see FIG. 2) between base ends 22, 24, and base passage 25 and cylinder passage 45 fluidly communicate with one another when cylinder 40 is coupled to base 20 to form infiltrometer passage 30, as illustrated. As illustrated in FIG. 1A, infiltrometer passage 30 is filled, at least in part, with water 14. Base end 22 of base 20 may be inserted into soil 12 (see FIG. 2) to allow water 14 to infiltrate into soil 12 through cylinder passage 45, through baffle 80, thence through at least portions of base passage 25 into soil 12, and exiting base end 22 to further infiltrate into soil 12.

As illustrated in FIG. 1C, slots, such as slot 47, are disposed about assembly side 62. When assembly side 62 of assembly 60 is placed upon second cylinder end 44, air may be communicated between assembly side 62 and second cylinder end 44 through slots, such as slot 47, into infiltrometer passage 30 in order to prevent vacuum formation within infiltrometer passage 30 as water 14 infiltrates into soil 12. Assembly arm 67 is in spaced relation with outer surface 41 of cylinder 40 to allow communication of air between assembly arm 67 and outer surface 41 into slots, such as slot 47. The slots are located in relation to second cylinder end 44 to communicate air between outer surface 41 and inner surface 42 of cylinder 40 (also see FIG. 4).

Assembly 60 includes level detector 69 to detect water surface level z of water surface 15 with respect to a reference including changes of water surface level z of water surface 15 with respect to time t, in this implementation. Assembly 60 is formed in a cylindrical shape with assembly side 62 removably couplable to second cylinder end 44 of cylinder 40, in this implementation, but assembly 60 could assume other geometric shapes in other implementations. As illustrated in FIGS. 1A, 1B, exemplary level detector 69 includes tube 70 that extends forth from assembly side 62 of assembly 60 through cylinder end 42 into cylinder passage 45, with tube end 72 positioned within infiltrometer passage 30. Level detector 69 may communicate data 94 indicative of the water surface level z of water surface 15 as a function of time z(t) including the rate of change of water surface level z of water surface 15 with respect to time (dz/dt) to computer 97 via network 99, and computer 97 may use data 94 to determine soil properties of soil 12. Network 99 may be wireless, at least in part.

Base 20 may be formed, for example, of stainless steel to allow insertion of end 22 of base 20 into soil 12 while preventing corrosion of base 20. Spacer 39 may be formed, for example, of stainless steel or rubber. Cylinder 40 may be formed, for example, of poly(methyl methacrylate) (PMMA), polycarbonate, borosilicate glass, or other transparent material, to allow a user to view water surface level z of water surface 15 within cylinder passage 45 of tube 40 concurrently with scale 19.

Baffle 80 is removably emplaced in infiltrometer passage 30 proximate base end 24 of base 20 and cylinder end 42 of cylinder 40, as illustrated in FIG. 1B, to prevent disturbance of soil 12 by the addition of water 14 to infiltrometer passage 30. In certain implementations, baffle 80 may be removed from infiltrometer passage 30 to allow infiltration of water 14 into soil 12 unimpeded by baffle 80. Baffle 80 may be removed from infiltrometer passage 30, for example, to allow the baffle 80, the infiltrometer passage 30, or both baffle 80 and infiltrometer passage 30 to be cleaned or to be stored separately.

FIG. 2 illustrates cylinder 40 coupled to base 20, baffle 80 emplaced in infiltrometer passage 30, and base 20 inserted into soil 12 to depth d. As illustrated in FIG. 2, portions of cylinder 40 proximate cylinder end 42 are coupled with base detent 27 of base 20 and with portions of spacer 39 that is in biased placement between cylinder end 42 and base 20. Portions of side 82 of baffle 80 rest upon other portions of spacer 39 that are not in biased placement between cylinder end 42 and base 20, as illustrated in FIG. 2, to position baffle 80 with respect to cylinder end 42 of cylinder 40 and base end 24 of base 20 within infiltrometer passage 30. Baffle side 83 of baffle 80 is in spaced relation with inner surface 43 of cylinder 40 to facilitate removal of baffle 80 from infiltrometer passage 30, as illustrated.

As illustrated in FIG. 2, face 28 of base detent 27 biases against soil surface 18 limiting the insertion of base 20 into soil 12 to depth d. Spacer 39 that is interposed between soil surface 18 and baffle side 82 of baffle 80 positions baffle 80 in infiltrometer passage 30, and spacer 39 cooperates with face 28 to define gap $L_1$ between soil surface 18 and baffle side 82, in this implementation. Thus, because of gap $L_1$, baffle 80 does not contact soil surface 18 during insertion of base 20 into soil or during addition of water 14 into infiltrometer passage 30, in this implementation. If baffle 80 is inserted into infiltrometer passage 30 following insertion of base 20 into soil 12, spacer 39 prevents contact between soil 12 and baffle 80, in this implementation. As disclosed herein, contact between baffle 80 and soil 12 is avoided because, for example, contact between baffle side 82 of baffle 80 and soil surface 18 may disturb soil surface 18 thus altering soil properties of soil 12 proximate soil surface 18. If baffle 80 is removed while base 20 is inserted into soil 12, spacer 39 prevents contact between baffle 80 and soil surface 18, in this implementation.

As illustrated in FIG. 2, grippable member 90 is secured to baffle 80, and grippable member 90 extends forth from baffle side 80 into cylinder passage 45. In this implementation, grippable member 90 is illustrated as a cord that extends through cylinder passage 45 and exits cylinder passage 45 at second cylinder end 44. Grippable member end 91 is secured to baffle 80 and grippable member end 93 (see FIG. 1B) extends forth from cylinder passage 45 through second cylinder end 44. The user may, for example, grasp grippable member 90 proximate grippable member end 93 and then remove baffle 80 from infiltrometer passage 30 by pulling baffle 80 out of infiltrometer passage 30 using grippable member 90.

While grippable member 90 is illustrated as a cord, a grippable member, such as grippable member 90, may be formed, for example, as a string, a chain, a wire, a handle, a loop, or an eyelet, in various implementations. The user may use various tools (not shown) such as a hook or a tong to grasp the grippable member or the baffle directly during removal of baffle 80 from infiltrometer passage 30, and the user may extend the various tool(s) into the infiltrometer passage 30 in order to grasp the grippable member or the baffle directly with the various tool(s) during removal of baffle 80.

Figure 3:
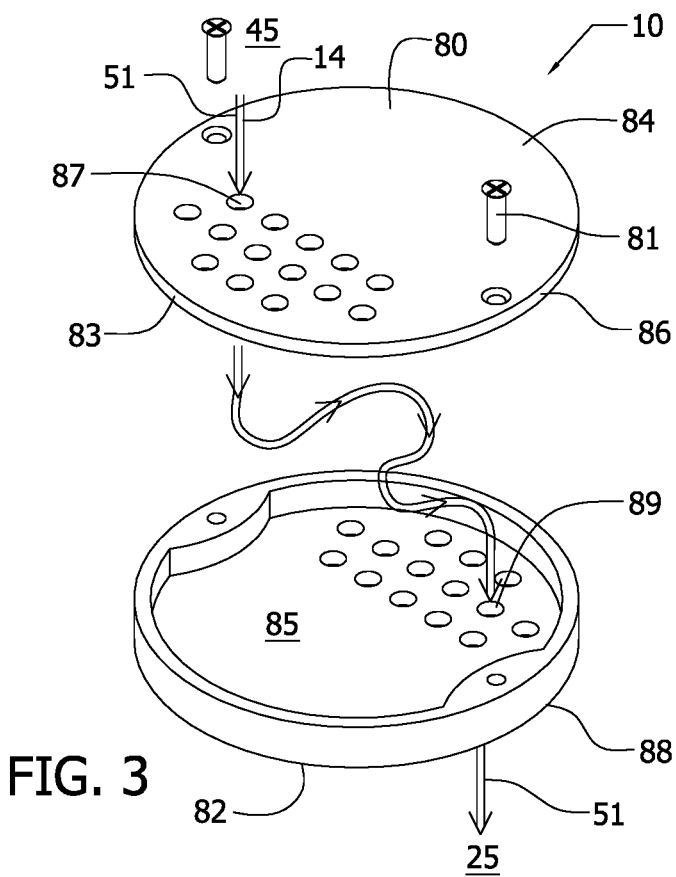
FIG. 3 illustrates by exploded perspective view portions of the exemplary infiltrometer apparatus of FIG. 1A.

FIG. 3 illustrates baffle segments 86, 88 that releasably interconnect with one another to form baffle 80. As illustrated, baffle segment 86 defines baffle side 84 and baffle segment 88 defines baffle side 82. Baffle segments 86, 88 define chamber 85 when interconnected, and holes, such as hole 87, in baffle side 84 are askew with respect to holes, such as hole 89, in baffle side 82 when baffle segments 86, 88 are interconnected, as illustrated. One or more removable fasteners, such as fastener 81, may be used to interconnect releasably baffle segments 86, 88. While fastener 81 is illustrated as a screw in this exemplary implementation, fastener 81 includes various other fasteners and detents, in other implementations, that releaseably interconnect baffle segments 86, 88.

With baffle segments 86, 88 interconnected and baffle 80 emplaced in infiltrometer passage 30 generally as illustrated in FIG. 2, water 14 poured into cylinder 40 at second cylinder end 44 flows into chamber 85 through holes, such as hole 87, in baffle side 84, through chamber 85, and from chamber 85 through holes, such as hole 89 in baffle side 82 into base passage 25 of base 20, as indicated by streamline 51 in FIG. 3. Flow of streamline 51 through holes, such as holes 87, 89, and through chamber 85 may dissipate energy of streamline 51 in order to prevent disturbance of soil surface 18 by streamline 51. Thus, in this implementation, baffle 80 quiets streamlines, such as streamline 51 including other fluidic disturbances to minimize disturbance of soil 12 including soil surface 18 as infiltrometer passage 30 of infiltrometer apparatus 10 is filled with water 14.

Figure 4:
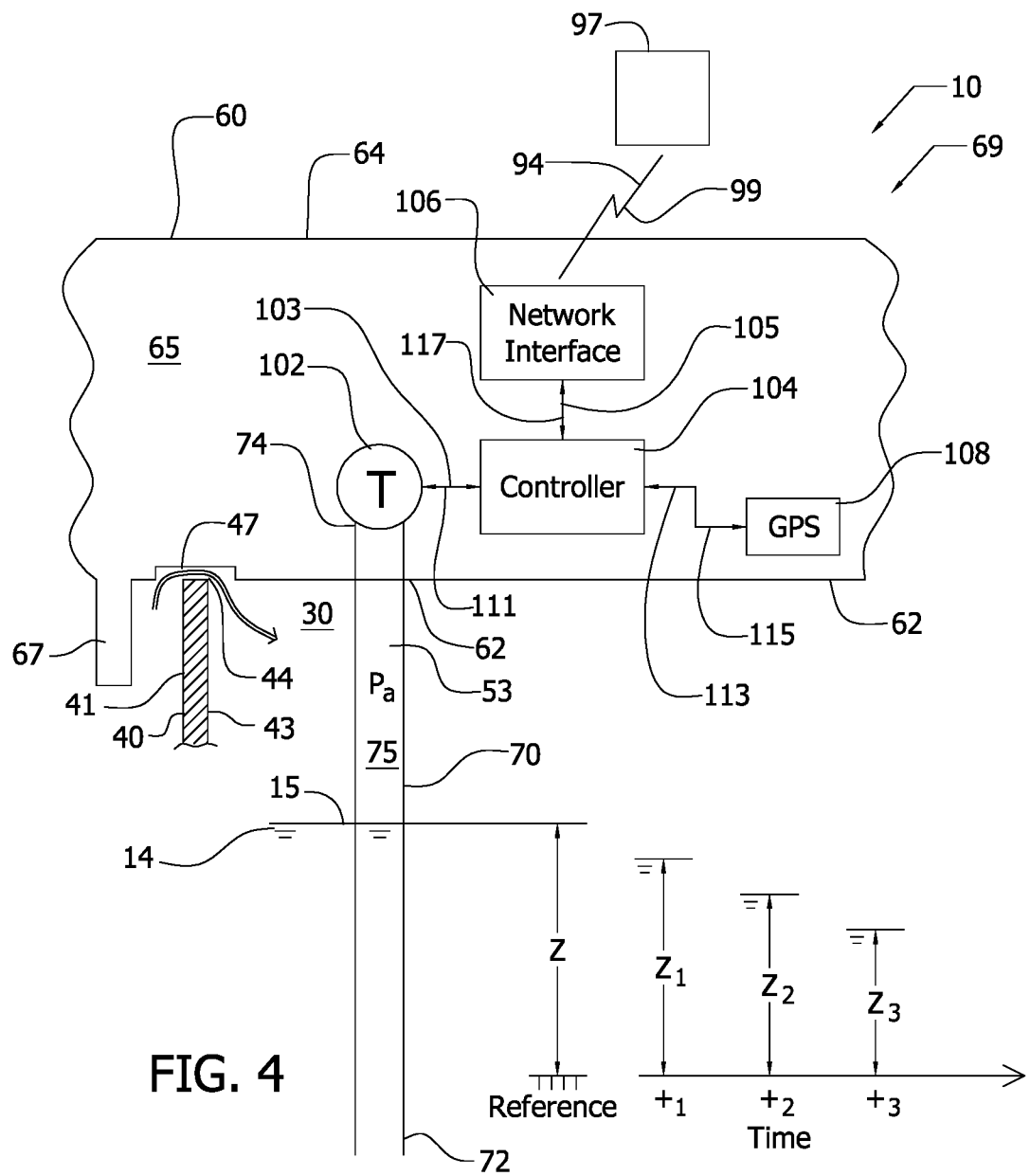
FIG. 4 illustrates by schematic diagram portions of the exemplary infiltrometer apparatus of FIG. 1A.

FIG. 4 illustrates assembly side 62 of assembly 60 placed upon second cylinder end 44 of cylinder 40. Air may be communicated between assembly arm 67 and outer surface 41 of cylinder through slots, such as slot 47, into infiltrometer passage 30 to prevent vacuum formation in infiltrometer passage 30. Note that cylinder end 44 contact assembly side 62 about slots, such as slot 47. Various structures may be provided about assembly side 62 to position cylinder end 44 with respect to the slots, such as slot 47, in various implementations.

FIG. 4 also illustrates level detector 69. As illustrated in FIG. 4, level detector 69 includes tube 70, pressure transducer 102, controller 104, network interface 106, and Global Positioning System (GPS) unit 108. Tube 70 forms tube passage 75 with water surface 15 at water surface level z within tube passage 75 and within infiltrometer passage 30 (assuming negligible surface tension within tube passage 75), as illustrated. Portions of tube passage 75 between water surface 15 and tube end 74 are occupied by air 53 at pressure $p_a$ that is compressed by the addition of water into infiltrometer passage 30, and pressure $p_a$ changes as water surface level z changes, in this implementation, i.e., the pressure $p_a$, which is greater than atmospheric pressure, decreases as water surface level z decreases due to infiltration of water 14 from infiltrometer passage 30 into soil 12 through soil surface 18. As illustrated, tube 70 communicates through assembly side 62 with tube end 74 in fluid communication with pressure transducer 102 to allow pressure transducer 102 to detect pressure $p_a$ of air 53 within tube passage 75. Because pressure $p_a$ is indicative of water surface level z, pressure transducer 102 detects the water surface level z by detecting pressure $p_a$ within tube passage 75 of tube 70, in this implementation.

As illustrated in FIG. 4, pressure transducer 102, controller 104, network interface 106, and GPS unit 108 are enclosed within assembly cavity 65 of assembly 60. Pressure transducer 102 is operatively coupled with controller 104 via communication pathway 103 and controller 104 is operatively coupled with network interface 106 via communication pathway 105, in this implementation. Pressure transducer 102 detects pressure $p_a$ and communicates signals 111 indicative of pressure $p_a$ to controller 104 via communication pathway 103, as illustrated. Controller 104 may communicate with pressure transducer 102 using communication pathway 103, for example, to direct the detection of pressure $p_a$ by pressure transducer 102 such as the frequency of detection of pressure $p_a$. Controller 104 may process signals 111 indicative of pressure $p_a$, and controller 104 may then communicate signals 117 with network interface 106 via communication pathway 105, and network interface 106 may then communicate data 94 with computer 97 via network 99. Data 94 and signals 117 may include signals 111 or be indicative of signals 111, and, thus, pressure transducer 102 may be linked with computer 97, in part, via network 99, in this implementation. Data 94 may be indicative of a plurality of water surface levels $z_1, z_2, z_3 \ldots$ at a corresponding plurality of times $t_1, t_2, t_3 \ldots$ detected by pressure transducer 102, as illustrated in FIG. 4.

As illustrated in FIG. 4, GPS unit 108 communicates signals 113 with controller 104 via communication pathway 115, and signals 113 are indicative, for example, of the GPS location at which the water surface levels $z_1, z_2, z_3 \ldots$ at corresponding times $t_1, t_2, t_3 \ldots$ are detected by pressure transducer 102. Data 94 and signals 117 may include signals 113 or be indicative of signals 113.

Computer 97 may communicate data 94 to network interface 106 via network 99, and network interface 106 may communicate signals 117 to controller 104 via communication pathway 105 to control operations of controller 104 including, for example, the detection of pressure $p_a$ by pressure transducer 102 as controlled by controller 104 or the detection of GPS location by GPS unit 108 as controlled by controller 104. Accordingly, computer 97 may communicate with level detector 69 via network 99 to control operations of level detector 69 including the detection of pressure $p_a$ by pressure transducer 102 or the detection of GPS location by GPS unit 108.

Controller 104 may include a microprocessor, A/D converter, D/A converter, clock, memory, power source, operatively received software, and so forth, as would be readily recognized by those of ordinary skill in the art upon study of this disclosure. In various implementations, for example, controller 104 may be an N550M8CC Integrated Circuit manufactured by Dynastream of Cochrane, AB, Canada that includes microprocessor, A to D conversion, and radio communications.

GPS unit 108 may be a GPS chip or other such device capable of receiving information, for example, from GPS satellites and calculating GPS location using that information. Although illustrated as a separate from controller 104 for explanatory purposes, network interface 106, GPS unit 108, or both network interface 106 and GPS unit 108 may be incorporated in controller 104. In other implementations, GPS unit 108 may be located in computer 97, and computer 97 may be proximate a location at which the water surface level z is being measured. Network interface 106 links communication pathway 105 with network 99 and may, for example, convert between digital signals transmissible over pathway 105 and digital signals transmissible over network 99, in this implementation. Data 94 and signals 111, 113, 117 may be analog, digital, or various combinations thereof, in various implementations. Communication pathways 103, 105, 115 may be wired, wireless, or combinations thereof, in various implementations. As would be understood by those of ordinary skill in the art upon study of this disclosure, various power source(s) such as a battery, power connector(s), data connector(s) such as an Ethernet port or a USB port, electrical transformers, power inverters, user interface(s), switche(s), electrical pathway(s), and so forth may be included in level detector 69 or disposed about assembly 60, in various implementations.

Figure 5A:
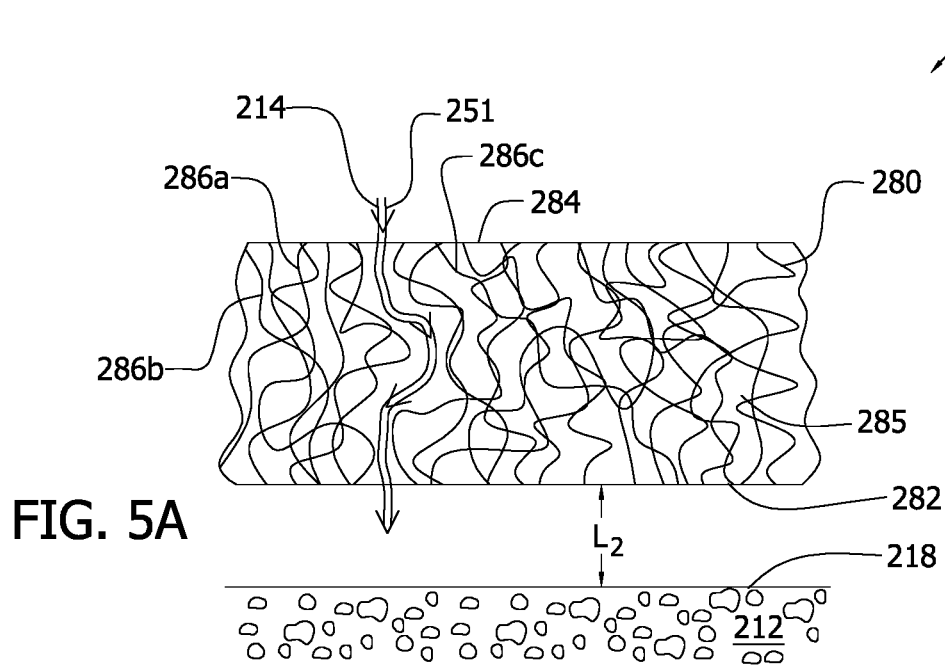
FIG. 5A illustrates by cut-away elevation view portions of a second exemplary implementation of an infiltrometer apparatus.

FIG. 5A illustrates portions of another exemplary implementation of an infiltrometer apparatus 200 including baffle 280. In this implementation, baffle 280 is formed of multiple strands, such as strands 286a, 286b, 286c, clumped together as a mesh 285. Strands, such as strands 286a, 286b, 286c, of mesh 285 may be formed of metal, such as stainless steel, or of various plastics, in various implementations. As illustrated, streamline 251 of water 214 passes between the strands, such as strands 286a, 286b, 286c, of mesh 285 as water 214 flows through baffle 280 from baffle side 284 to baffle side 282. The flow of streamlines, such as streamline 251, about the strands may reduce the energy of streamline 251 in order to prevent disturbance of soil surface 218 of soil 212 by streamlines, such as streamline 251, created as infiltrometer apparatus 200 is filled with water 214. Note that baffle side 282 is offset from soil surface 218 by gap $L_2$, as contact between baffle 280 and soil 212, such as contact between side 282 and soil surface 218, may disturb soil 212 thereby altering the soil properties of soil 212.

Figure 5B:
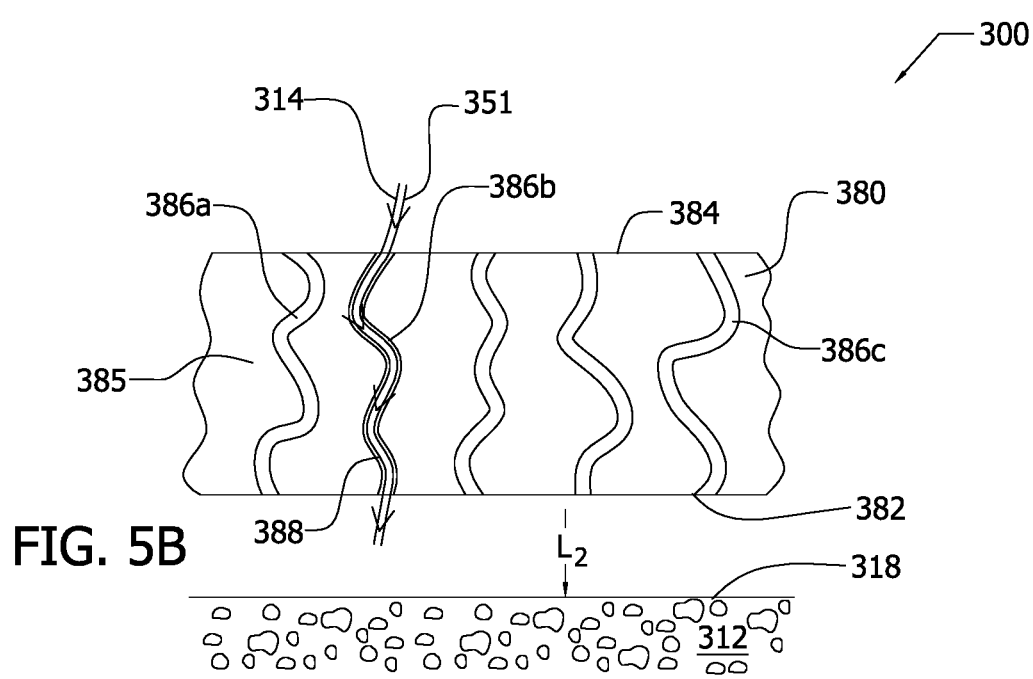
FIG. 5B illustrates by cut-away elevation view portions of a third exemplary implementation of an infiltrometer apparatus; and, FIG. 6 illustrates by schematic diagram portions of a fourth exemplary implementation of an infiltrometer apparatus.

FIG. 5B illustrates portions of another exemplary implementation of an infiltrometer apparatus 300 including baffle 380. In this implementation, baffle 380 is formed of porous material 385. Pores, such as pores 386a, 386b, 386c, of porous material 385 pass between baffle sides 382, 384 in a tortuous manner, as illustrated. Accordingly, as illustrated, streamlines, such as streamline 351, of water 314 flow through pores, such as pores 386a, 386b, 386c, as water 314 flows through baffle 380 from baffle side 384 to baffle side 382 during filling of infiltrometer apparatus 300. The flow of streamlines, such as streamline 351, through the pores, such as pores 386a, 386b, 386c, may reduce the energy of the streamlines and damp various fluidic disturbances in order to prevent disturbance of soil 312 as infiltrometer apparatus 300 is filled with water 314. Note that baffle side 382 is offset from soil surface 318 of soil 312 by gap $L_3$, as contact between baffle 380 and soil 312, such as between baffle side 382 and soil surface 318, may disturb soil 312 proximate soil surface 318 thereby altering the soil properties of soil 312. Porous material 385 may be, for example, formed, for example, of polyvinyl chloride (PVC), acrylonitrile butadiene styrene (ABS), polypropylene, polycarbonate, bakelite, nylon, high-density polyethylene (HDPE), or low-density polyethylene.

Figure 6:
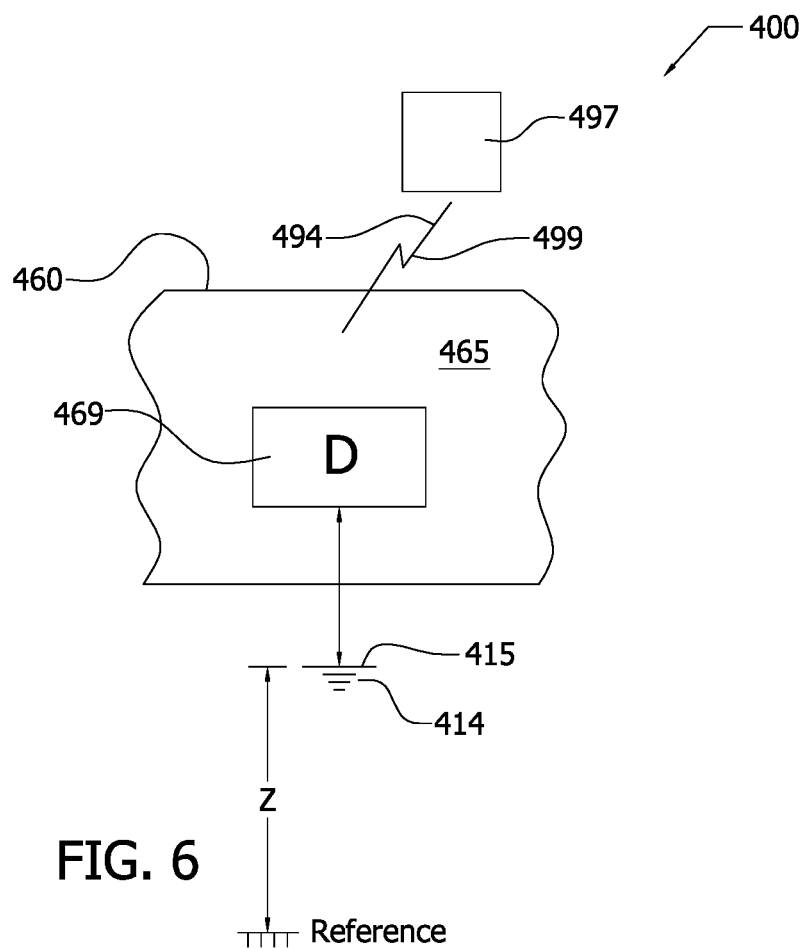

FIG. 6 illustrates portions of another exemplary implementation of an infiltrometer apparatus 400 including level detector 469 located within assembly cavity 465 of assembly 460, and computer 497. As illustrated, level detector 469 cooperates with water surface 415 of water 414 to detect water surface level z as a function of time t as water 414 infiltrates into soil, such as soil 12, 212, 312. In various implementations, level detector 469 may detect water surface level z as a function of time t using, for example, a float, a laser, an infrared sensor, SONAR, triangulation, machine vision, or a wave probe (either capacitive or resistive). Level detector 469 communicates data 494 indicative of water surface level z as a function of time t to computer 497 via network 499, as illustrated.

In operation, an infiltrometer apparatus, such as infiltrometer apparatus 10, 200, 300, 400 is used to measure soil properties of a soil, such as soil 12, 212, 312. A cylinder end of a cylinder, such as cylinder end 42 of cylinder 40, is coupled with a base end of a base, such as base end 24 of base 20 to align base passage, such as base passages 25, with cylinder passage, such as cylinder passage 45, and in fluid communication with one another thus forming an infiltrometer passage, such as infiltrometer passage 30.

A base end, such as base end 22, of the base is then inserted into the soil to depth d with the infiltrometer passage generally oriented vertically. Following insertion of the base into the soil, a baffle side, such as baffle side 82, 282, 382, of a baffle, such as baffle 80, 280, 380, emplaced within the infiltrometer passage is offset from a soil surface, such as soil surface 18, 218, 318, by a gap, such as gap $L_1$, $L_2$, $L_3$. Thus, the baffle does not contact the soil surface during insertion of the base into the soil or following insertion of the base into the soil. The base may be formed, for example with face 28, to limit the depth that the base may be inserted into the soil. In some implementations, the baffle may be removably placed within the infiltrometer passage prior to insertion of the base into the soil, while, in other implementations, the baffle may be removably placed within the infiltrometer passage following insertion of the base into the soil, in both implementations the gap is maintained between the baffle and the soil surface.

With the base inserted into the soil and the baffle emplaced within the infiltrometer passage, water, such as water 14, 214, 314, 414, is then added into the infiltrometer passage through, for example, second cylinder end 44, filling at least portions of the infiltrometer passage above the soil surface. The baffle may, for example, damp turbulence and other fluidic perturbations and dissipate energy during filling of the infiltrometer passage thereby preventing disturbance of the soil by filling of the infiltrometer passage that may alter soil properties of the soil as may be measured by the infiltrometer apparatus. Accordingly, the baffle may eliminate certain measurement errors caused by disturbance of the soil during filling of the infiltrometer passage.

After filling the infiltrometer passage sufficiently, an assembly, such as assembly 60, 460 that includes a level detector, such as level detector 69, 469, may be placed upon a cylinder end, such as second cylinder end 44, of the cylinder. In some implementations of the assembly, portions of the level detector may be inserted into the cylinder passage concurrently with coupling of the assembly to the cylinder. For example, in certain implementations of the level detector, a tube, such as tube 70, is inserted into the cylinder passage concurrently with coupling of the assembly to the cylinder.

As water infiltrates into the soil from the base, the level detector detects the water surface level z of a water surface, such as water surface 15, 415, within the infiltrometer passage. For example, in some implementations of the level detector, a pressure transducer, such as pressure transducer 102, detects pressure $p_a$ in a tube passage, such as tube passage 75, of the tube, the pressure $p_a$ being indicative of the water surface level z within the infiltrometer passage. Air may be communicated through slots, such as slot 47, into the cylinder passage to prevent vacuum formation within the infiltrometer passage as the water surface level z decreases.

The level detector may then communicate data, such as data 94, 494 with a computer, such as computer 97, 497, via a network, such as network 99, 499. For example, in some implementations, the pressure transducer may cooperate with a controller, such as controller 104, and with a network interface, such as network interface 106, to communicated data with the computer via the network. The data may be indicative of the water surface level z within the cylinder passage, for example, as a function of time z(t). The data may be indicative of a rate of change of the water surface level of the water surface with respect to time (dz/dt). The computer may record the data, which may include a plurality of water surface levels $z_1$, $z_2$, $z_3$ . . . at a corresponding plurality of times $t_1$, $t_2$, $t_3$ . . . , and the computer may use the data to determine soil properties of the soil. Various software may be operatively received by the computer to determine soil properties of the soil from the plurality of water surface levels $z_1$, $z_2$, $z_3$ . . . at the corresponding plurality of times $t_1$, $t_2$, $t_3$ . . . . The data communicated to the computer may include signals, such as signals 113, indicative of the GPS location at which the water surface level z is being measured. In other implementations, the computer may determine the GPS location of the computer, the computer being proximate to the location at which the data indicative of the water surface level z as a function of time is obtained. The computer may record the GPS location, and the computer may associate the data indicative of the water surface level z as a function of time, the soil properties determined from the data indicative of the water surface level z as a function of time, and the GPS location. The computer may aggregate data indicative of the water surface level z as a function of time and corresponding soil properties at a plurality of GPS locations thereby mapping soil properties within some geographic region. The computer may communicate with the level detector via the network, for example, to control, at least in part, the detection of the water surface level z as a function of time such as, for example, the times $t_1$, $t_2$, $t_3$ . . . at which water surface levels $z_1$, $z_2$, $z_3$ . . . are measured.

In various implementations, after filling of at least portions of infiltrometer passage, the baffle may either be removed from the infiltrometer passage or the baffle may remain within the infiltrometer passage as water is infiltrated into the soil during measurement of z(t). A user may grasp a grippable member, such as grippable member 90, and may then remove the baffle from the interface passage, at least in part, using the grippable member.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. This Abstract is not intended to identify key elements of the apparatus and methods disclosed herein or to delineate the scope thereof. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A falling head infiltrometer apparatus, comprising:
   a cylinder that defines a cylinder passage;
   a base that defines a base passage, the base coupleable to a first cylinder end of the cylinder to form an infiltrometer passage;
   a baffle removably emplacable within the infiltrometer passage and received at least in part by the base, the baffle decreases disturbance of soil by addition of water into the infiltrometer passage;
   an assembly removably coupleable to a second cylinder end of the cylinder opposite the base, the assembly comprising a level detector to detect a water surface level of a water surface within the infiltrometer passage, the level detector linkable by network with a computer to communicate data indicative of the water surface level to the computer, the level detector further comprises a tube extendable into the infiltrometer passage from the assembly, the level detector further comprises a pressure transducer in fluid communication with a tube passage of the tube to detect air pressure $p_a$ within the tube passage; and
   wherein the cylinder is coupled in vertical axial alignment with the base to form a unitary structure when said failing head infiltrometer apparatus is deployed, and water flows through the baffle continuously from the infiltrometer passage toward a soil surface of the soil without interruption throughout an entirety of a falling head infiltration test conducted using said falling head infiltrometer apparatus.

2. The apparatus of claim 1, the baffle comprising:
   a baffle segment defining a set of holes therethrough;
   a second baffle segment defining a second set of holes therethrough, the second baffle segment interconnectable with the baffle segment to define a baffle chamber, the set of holes being askew of the second set of holes when the baffle segment and second baffle segment are interconnected.

3. The apparatus of claim 1, the baffle comprising multiple strands of material clumped together forming a mesh.

4. The apparatus of claim 1, the baffle comprising a porous material.

5. The apparatus of claim 1, further comprising:
   a grippable member attached to the baffle to allow removal of the baffle from the infiltrometer passage.

6. The apparatus of claim 1, the base comprising a structure that limits insertion of the base into the soil.

7. The apparatus of claim 1, further comprising:
   a spacer received within the infiltrometer passage to maintain, at least in part, the spaced relation between the baffle and the soil surface.

8. The apparatus of claim 1, the cylinder and the base are permanently coupled to one another.

9. The apparatus of claim 1, the data further comprising a plurality of water surface levels at a corresponding plurality of times.

10. The apparatus of claim 1, the network comprising wireless communication technologies.

11. The apparatus of claim 1, wherein the air pressure $p_a$ being indicative of the water surface level z within the infiltrometer passage.

12. A falling head infiltrometer apparatus, comprising:
    a cylinder;
    a base coupleable to a first cylinder end of the cylinder to form an infiltrometer passage, the base insertable into a soil to support said falling head infiltrometer apparatus;
    a baffle removably emplacable within the infiltrometer passage and received at least in part by the base;
    an assembly removably coupleable to a second cylinder end of the cylinder opposite the base, the assembly comprising a level detector to detect a water surface level of a water surface within the infiltrometer passage,
    the level detector linkable by network with a computer to communicate data indicative of the water surface level to the computer the level detector further comprises a tube extendable into the infiltrometer passage from the assembly, the level detector further comprises a pressure transducer in fluid communication with a tube passage of the tube to detect air pressure $p_a$ within the tube passage; and
    wherein the cylinder is coupled in vertical axial alignment with the base and the cylinder is coupled in vertical axial alignment with the assembly to form a unitary structure when said failing head infiltrometer apparatus is inserted into the soil.

13. The apparatus of claim 12, wherein the air pressure $p_a$ being indicative of a water surface level of a water surface within the infiltrometer passage, the pressure transducer linkable by network with a computer to communicate data indicative of the water surface level to the computer.

14. The apparatus of claim 12, the network comprising wireless communication technologies.

15. The apparatus of claim 12, the data further comprising a plurality of water surface levels at a corresponding plurality of times.

16. A falling head infiltrometer apparatus in deployment, comprising:
    a cylinder;
    a base coupled to a first cylinder end of the cylinder in vertical axial alignment with the cylinder to form a unitary structure that defines an infiltrometer passage, and the base inserted into a soil;
    a baffle emplaced within the infiltrometer passage to decrease disturbance of the soil by addition of water into the infiltrometer passage; and
    an assembly coupled to a second cylinder end of the cylinder opposite the base, the assembly comprising a level detector to detect a water surface level of a water surface within the infiltrometer passage, the level detector further comprises a tube extending into the infiltrometer passage from the assembly, the level detector further comprises a pressure transducer in fluid communication with a tube passage of the tube to detect air pressure $p_a$ within the tube passage.

17. The apparatus of claim 16, wherein the level detector is linked by network to communicate data indicative of the water surface level to a computer.

* * * * *